United States Patent
Dillon (10) Patent No.: US 8,734,327 B2
(45) Date of Patent: May 27, 2014

(54) DEVICE PLATFORM FOR MEDICAL PROCEDURES

(75) Inventor: Travis E. Dillon, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 772 days.

(21) Appl. No.: 12/429,383

(22) Filed: Apr. 24, 2009

(65) Prior Publication Data

US 2009/0270677 A1 Oct. 29, 2009

Related U.S. Application Data (60) Provisional application No. 61/048,647, filed on Apr. 29, 2008.

(51) Int. Cl.
*A61B 1/04* (2006.01)
*A61B 1/00* (2006.01)

(52) U.S. Cl.
CPC ................................. *A61B 1/0014* (2013.01)
USPC ............ 600/106; 600/102; 600/104; 600/107

(58) Field of Classification Search
CPC ............... A61B 19/26; A61B 1/00121; A61B 1/00128; A61B 1/0014; A61B 1/00147; A61B 1/00154
USPC ........................ 600/106, 102, 107, 114; 606/1
See application file for complete search history.

(56) References Cited

U.S. PATENT DOCUMENTS

| 4,696,544 | A | * | 9/1987 | Costella | 600/114 |
| 5,607,386 | A | * | 3/1997 | Flam | 600/114 |
| 6,193,736 | B1 | * | 2/2001 | Webler et al. | 606/171 |
| 6,520,954 | B2 | * | 2/2003 | Ouchi | 606/1 |
| 2006/0041245 | A1 | | 2/2006 | Ferry et al. | |
| 2007/0152420 | A1 | * | 7/2007 | DeLong et al. | 280/230 |
| 2008/0243176 | A1 | * | 10/2008 | Weitzner et al. | 600/114 |

FOREIGN PATENT DOCUMENTS

| EP | 1582139 | | 10/2005 | | |
| JP | 2001-054255 | | 2/2001 | | |
| JP | 2001-170063 | | 6/2001 | | |
| JP | 2001170063 | A | * | 6/2001 | ............. A61B 17/34 |

OTHER PUBLICATIONS

International Search Report and Written Opinion for PCT/US2009/041610 mailed Aug. 27, 2009.
International Preliminary Report on Patentability for PCT/US2009/041610 mailed Aug. 5, 2010, 8 pgs.

* cited by examiner

*Primary Examiner* — Matthew J Kasztejna
*Assistant Examiner* — Kevin G Barry, III
(74) *Attorney, Agent, or Firm* — Brinks Gilson & Lione (57) ABSTRACT

The present embodiments provide apparatus and methods suitable for facilitating positioning one or more medical components. In one embodiment, the apparatus comprises a rail member having proximal and distal ends and a generally longitudinal axis. A first connector is adapted to be selectively coupled to the rail member, and a first medical component is adapted to be coupled to the first connector. The first connector is disposed for selective longitudinal movement along the rail member, thereby permitting movement of the first medical component with respect to the rail member. In this manner, one or more components, such as a catheter and a needle, may be inserted into a human or animal body in a controlled fashion with respect to one another.

17 Claims, 8 Drawing Sheets

DEVICE PLATFORM FOR MEDICAL PROCEDURES

PRIORITY CLAIM

This invention claims the benefit of priority of U.S. Provisional Application Ser. No. 61/048,647, entitled "Device Platform for Medical Procedures," filed Apr. 29, 2008, the disclosure of which is hereby incorporated by reference in its entirety.

TECHNICAL FIELD

The present embodiments relate generally to the field of medical devices, and more particularly, to apparatus and methods for facilitating positioning of one or more medical components.

BACKGROUND INFORMATION

Medical components may be advanced into the human or animal body for a wide range of diagnostic and therapeutic purposes. For example, catheters, needles, extraction baskets, stents, snares and numerous other components may be inserted into a patient's vasculature, gastric system, or other ducts or passageways in order to facilitate imaging and/or treatment of various conditions.

The medical components may be inserted and advanced through an outer cover, sheath, endoscope or similar introducer device. In the case of an endoscopic procedure, an endoscope may be advanced towards a target site using an imaging system, and one or more medical components may be advanced through a working lumen of the endoscope towards the target site.

There are instances in which multiple medical components may be used in a series of smaller procedures during a single, larger operation. For example, in a "rendezvous procedure," a combination of one or more smaller procedures may be performed such as the injection of a radiopaque dye, cannulation of a passageway, drainage of a cyst, delivery of a therapeutic agent to a target site, the use of fine needle aspiration to obtain tissue or fluid samples, dilation of a target site, insertion of a stent, and so forth.

It may become difficult to precisely position a medical component within a patient's vessel or duct, particularly when multiple components are used at the same time. Moreover, incremental longitudinal advancement or retraction of the multiple medical components with respect to each other may become difficult to achieve. Furthermore, it may become difficult to exchange one medical component for another.

Accordingly, there is a need for apparatus and methods that facilitate insertion and/or positioning of one or more medical components, such that improved positioning of the medical components may be achieved in an easy-to-use manner.

SUMMARY

The present embodiments provide apparatus and methods suitable for facilitating positioning one or more medical components. In one embodiment, the apparatus comprises a rail member having proximal and distal ends and a generally longitudinal axis. A first connector is adapted to be selectively coupled to the rail member, and a first medical component is adapted to be coupled to the first connector. The first connector is disposed for selective longitudinal movement along the rail member, thereby advancing or retracting the first medical component upon corresponding movement of the first connector.

The apparatus may further comprise a second connector adapted to be coupled to the rail member and a second component. The second connector is disposed for selective longitudinal movement along the rail member, thereby advancing and retracting the second medical component upon corresponding movement of the second connector. The second connector is configured for independent longitudinal movement relative to the first connector.

An adapter may be coupled to the distal end of the rail member, and further may be coupled to a port of an introducer device, such as an endoscope, in order to align the first connector with the port of the introducer device to facilitate insertion of the first medical component into the introducer device. The rail member may comprise measurement indicia for identifying a longitudinal distance in which the first connector and the first medical component have been advanced or retracted with respect to the rail member. In this manner, one or more components, such as a catheter and a needle, may be inserted into a human or animal body in a controlled fashion with respect to one another.

The first and second connectors each may comprise a rail engaging portion and a component engaging portion. The rail engaging portion may comprise a bore having a greater diameter than an outer diameter of the rail member to permit movement of the connectors over the rail member. The rail engaging portion of the connectors also may comprises a guide member adapted for movement within a slot formed in the rail member, thereby substantially inhibiting rotational movement of the connectors with respect to the rail member. An actuator, such as a thumb screw, may be provided for selectively inhibiting longitudinal movement of the connectors with respect to the rail member, thereby securing the longitudinal positioning of the first and second medical components.

The component engaging portion of the first and second connectors each may comprise a bore adapted to receive a proximal end of the first medical component. The first and second medical components are adapted to be securely connected to the component engaging portion, for example, using an actuator such as a thumb screw.

In one exemplary method of operation, the introducer device may comprise an endoscope having an accessory port that enables insertion of first and second medical components into a working lumen of the endoscope. In one embodiment, the first medical component may comprise a catheter having a lumen, and the second medical component may comprise a needle adapted to be advanced through the lumen of the catheter. The catheter and the needle may be advanced through the working lumen of the endoscope to a target site. Advantageously, using the rail member in conjunction with first and second connectors, the first and second medical components may be independently advanced a fixed amount with respect to one another, and with respect to the endoscope, to perform the objectives of a particular procedure.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION OF THE PREFERRED EMBODIMENTS

In the present application, the term "proximal" refers to a direction that is generally towards a physician during a medical procedure, while the term "distal" refers to a direction that is generally towards a target site within a patient's anatomy during a medical procedure.

Figures 1, 2:
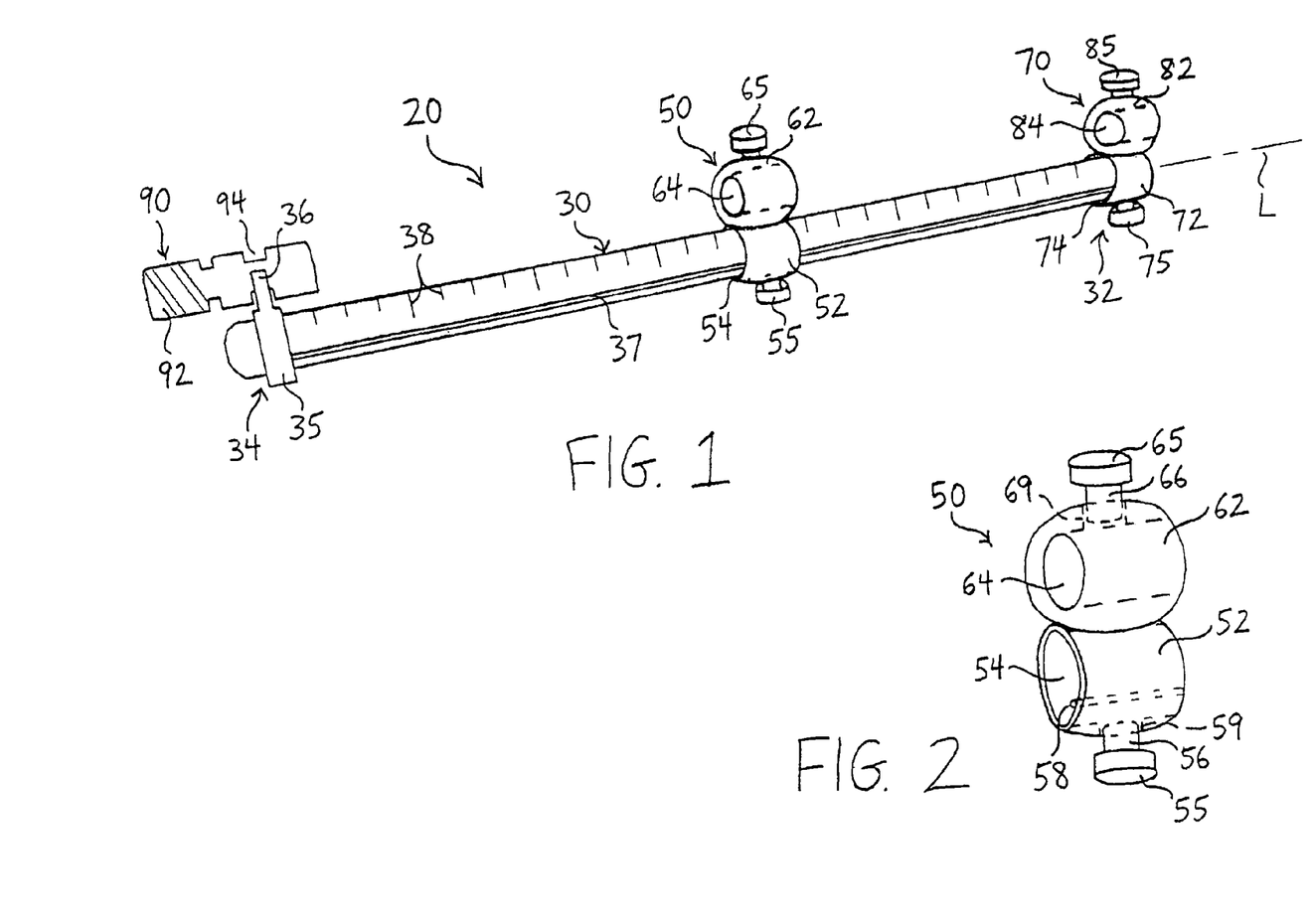
FIG. 1 is a perspective view of a first embodiment of apparatus for facilitating positioning of one or more medical components.
FIG. 2 is a perspective view illustrating features of a connector of FIG. 1.

Referring now to FIG. 1, a first embodiment of apparatus suitable for facilitating insertion of one or more medical components is described. The apparatus 20 generally comprises a rail member 30 having proximal and distal ends 32 and 34, respectively, and a generally longitudinal axis L. The apparatus 20 further comprises at least a first connector 50, which is adapted for longitudinal movement with respect to the rail member 30, as set forth in greater detail below.

The first connector 50 may comprise a rail engaging portion 52 and a component engaging portion 62, as shown in FIG. 2. The rail engaging portion 52 may comprise a substantially hollow member having a bore 54 formed therethrough. The bore 54 may comprise a diameter that may be slightly greater than an outer diameter of the rail member 30. Accordingly, the rail engaging portion 52 of the first connector 50 may be disposed over, and slide along, the rail member 30, as generally depicted in FIG. 1.

The rail member 30 may comprise a generally cylindrical cross-sectional shape, as depicted in FIG. 1. If the rail member 30 comprises a generally cylindrical shape, then the bore 54 of the rail engaging portion 52 also may comprise a generally cylindrical shape to permit selective longitudinal movement of the first connector 50 with respect to the rail member 30. In alternative embodiments, the rail member 30 may comprise other suitable exterior shapes, such as an oval or rectangular cross-sectional shape, in which case the bore 54 of the rail engaging portion 52 may comprise a corresponding interior shape.

In one embodiment, the rail engaging portion 52 may comprise a guide member 58, which may be longitudinally oriented and disposed within the bore 54, as shown in FIG. 2. The guide member 58 may be disposed for longitudinal movement within a longitudinally oriented slot 37 formed in a lateral surface of the rail member 30, as depicted in FIG. 1. Accordingly, the guide member 58 may permit longitudinal movement of the first connector 50 with respect to the rail member 30, while substantially inhibiting rotational movement of the first connector 50 with respect to the rail member 30.

The first connector 50 further may comprise a mechanism for securing its longitudinal movement with respect to the rail member 30. In one embodiment, the mechanism comprises a thumb screw 55 having a threaded portion 56, as shown in FIGS. 1-2. The threaded portion 56 may be coupled to a bore 59 having internal threading, thereby allowing incremental adjustment of the positioning of the thumb screw 55 within the bore 54 of the rail engaging portion 52. The thumb screw 55 may be actuated such that the threaded portion 56 is disposed within the bore 54, thereby engaging an outer surface of the rail member 30 and inhibiting longitudinal movement of the first connector 50 with respect to the rail member 30.

The first connector 50 further comprises a component engaging portion 62, which may comprise features that are similar to the rail engaging portion 52. More specifically, the component engaging portion 62 may comprise a substantially longitudinally oriented bore 64 formed therein, as shown in FIGS. 1-2. The bore 64 may be configured for receiving a proximal portion of one or more medical components, as explained in further detail below. The first connector 50 also may comprise a mechanism for securing a medical component within the bore 64 of the component engaging portion 62. In one embodiment, a thumb screw 65 having a threaded portion 66 may be coupled to a bore 69 having internal threading, as shown in FIG. 2. The thumb screw 65 may be incrementally positioned within the bore 64 of the component engaging portion 62 to engage and effectively secure a medical component positioned therein, as explained further below.

In the embodiments shown herein, the apparatus 20 comprises the first connector 50 and also a second connector 70. Unless otherwise noted, the first and second connectors 50 and 70 are substantially identical. The first connector 50 may be coupled to the proximal end of a first medical component, while the second connector 70 may be coupled to the proximal end of a second medical component. As will be explained further below, the first and second connectors 50 and 70 may be longitudinally positioned with respect to each other, via the rail member 30, to thereby incrementally longitudinally position the first medical component with respect to the second medical component as well as with respect to the endoscope 110. While two connectors 50 and 70 are depicted, greater or fewer connectors may be used at any time in conjunction with the rail member 30 to facilitate positioning of one or more medical components.

Figure 3:
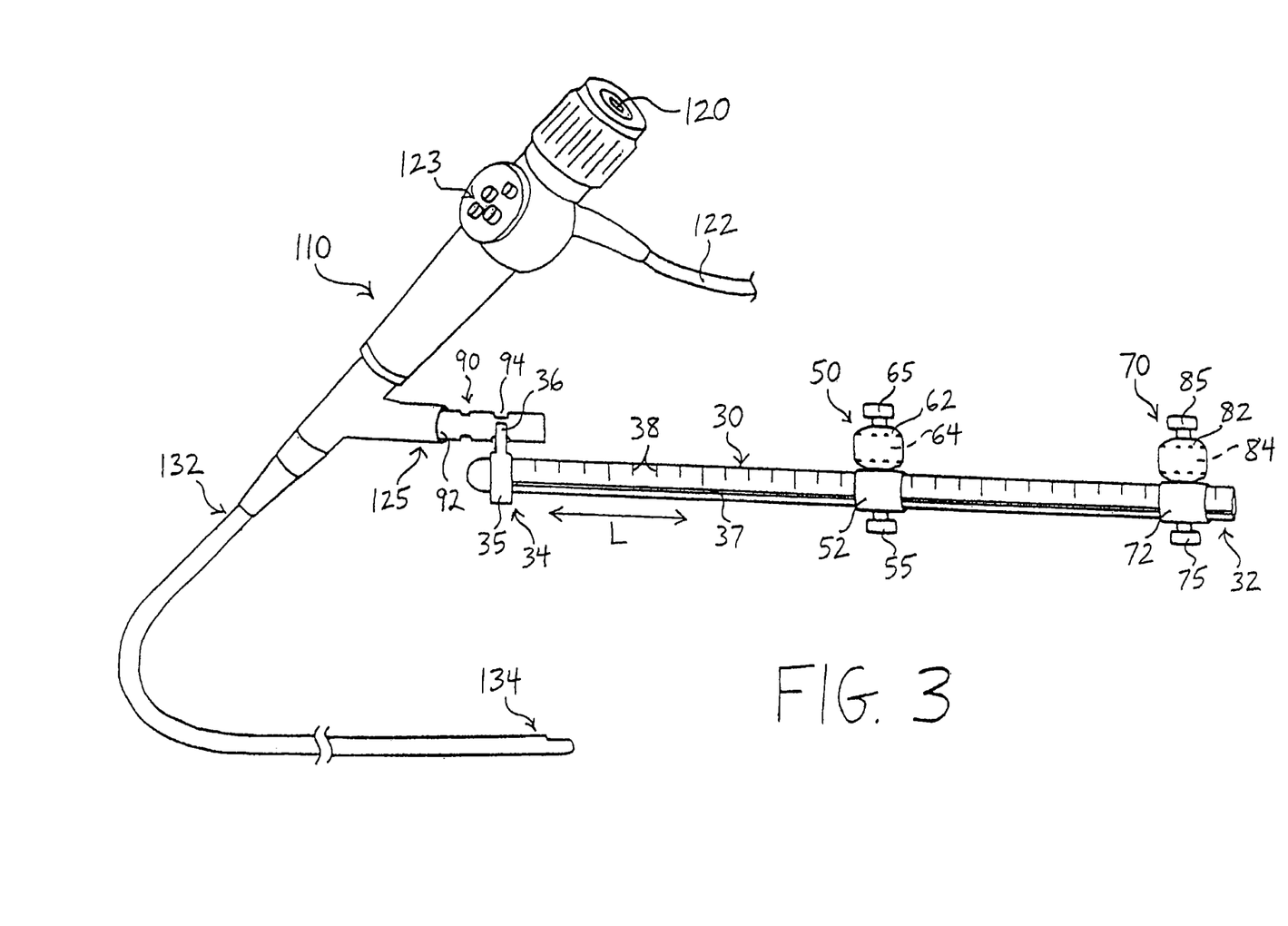
FIG. 3 is a perspective view showing the apparatus of FIG. 1 coupled to an accessory port of an endoscope.

The apparatus 20 further may comprise an adapter 90, which may couple the distal end 34 of the rail member 30 to an introducer device, such as an endoscope 110, as shown in FIG. 3. The adapter 90 may comprise any suitable shape configured to couple the rail member 30 to the introducer device. By way of example, the adapter 90 may comprise a male luer lock adapter having a distal region 92, which may be removably coupled to an accessory port 125 of the endoscope 110, as shown in FIG. 3.

Further, the apparatus 20 may comprise a fitting 35, which is adapted to be coupled between the adapter 90 and the rail member 30, as shown in FIG. 3. The fitting 35 may be removably or permanently coupled to the distal end 34 of the rail member 30. The fitting 35 may comprise a C-shaped clip 36, shown substantially from the side in FIG. 3, that is adapted to be coupled to a notch 94 formed in the adapter 90. When the C-shaped clip 36 is secured within the notch 94, e.g., using a snap-fit connection, the rail member 30 may be securely coupled to the adapter 90 and also the endoscope 110. While a C-shaped clip 36 is depicted in FIG. 1 and FIG. 3, any suitable mechanism may be used for removably coupling the rail member 30 to the adapter 90.

The rail member 30 may be coupled to the accessory port 125 of the endoscope 110 such that the bores 64 and 84 of the first and second connectors 50 and 70, respectively, are substantially aligned with the adapter 90, as shown in FIG. 3. Therefore, when medical components are secured within the bores 64 and 84 of the first and second connectors 50 and 70, respectively, the first and second connectors 50 and 70 may be longitudinally advanced over the rail member 30 to longitudinally advance the medical components through the adapter 90 and into a working lumen 128 of the endoscope 110, as explained further below.

The rail member 30 may be formed from any suitable material, such as plastic or stainless steel. The overall longitudinal length of the rail member 30, i.e., the length between the proximal end 32 and the distal end 34, may comprise any suitable length for permitting movement of one or more connectors along the rail member 30. In one embodiment, the longitudinal length of the rail member 30 may be about 20 to about 30 centimeters. Further, the rail member 30 may comprise measurement indicia 38, which may allow a physician to know exactly how far the first and second connectors 50 and 70 are moved with respect to the endoscope 110 and further with respect to one another.

The apparatus 20 may be used in conjunction with any suitable introducer device, such as the endoscope 110 shown in FIG. 3. The exemplary endoscope shown comprises a side-viewing endoscope 110 having proximal and distal ends 132 and 134, respectively. The endoscope 110 may comprise fiber optic components for illuminating and capturing an image distal to the endoscope 110. A physician may view the images distal to the endoscope using an eyepiece 120. A fiber optic cable 122 may be coupled between the endoscope 110 and a suitable light source. A control section 123 may be provided to facilitate actuation of various components associated with the endoscope 110.

Figures 4, 5:
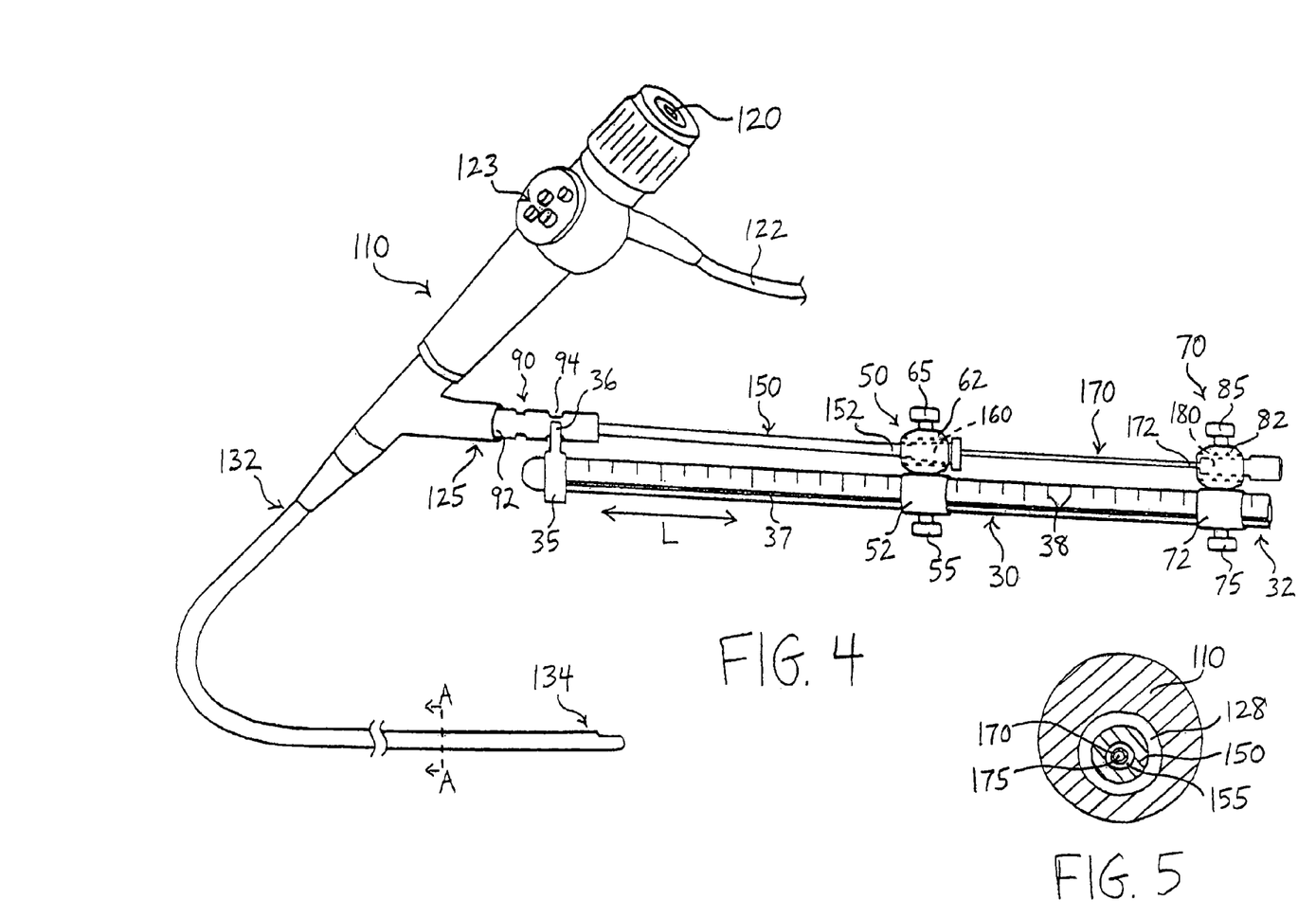
FIG. 4 is a perspective view showing exemplary first and second medical components being used in conjunction with the apparatus of FIGS. 1-3.
FIG. 5 is a cross-sectional view along line A—A of FIG. 4.

Further, the endoscope 110 may comprise a working lumen 128, as shown in FIG. 5. The working lumen 128 is sized to accommodate at least one medical component therein, as generally described with respect to FIGS. 4-10. An adjustable guiding element may be disposed near the distal end 134 of the endoscope 110 to cause components advanced through the working lumen 128 to exit at a predetermined angle with respect to the endoscope 110. It should be noted that, for illustrative purposes, the optical components associated with the endoscope 110 are not shown in the cross-sectional view of FIG. 5.

Optionally, an endoscopic ultrasound procedure may be performed, in which case the endoscope 110 may be retrofitted with an ultrasound transducer. The ultrasound transducer may produce accurate and detailed images of the digestive tract and surrounding organs, particularly due to the proximity of the ultrasound transducer to the organ or tract being imaged.

Referring now to FIGS. 4-8, a first exemplary method of using the apparatus 20 is described. In a first step, the rail member 30 may be coupled to the accessory port 125 of the endoscope 110, as generally set forth above. In one embodiment, the rail member 30 may be coupled to the adapter 90 by coupling the C-fitting 36 to the notch 94 of the adapter 90. Other techniques or mechanisms may be employed to couple the rail member 30 to the endoscope 110.

In a next step, proximal ends of one or more medical components, such as a dilation catheter 150 and a needle 170, may be coupled to the first and second connectors 50 and 70, respectively. It should be noted that the dilation catheter 150 may be coupled to the first connector 50 before the first connector 50 is secured to the rail member 30, and similarly, the needle 170 may be coupled to the second connector 70 before the second connector 70 is secured to the rail member 30, which may facilitate the loading process.

In one exemplary step, a proximal end 152 of the dilation catheter 150 may be coupled to the first connector 50, for example, using a luer fitting 160. The luer fitting 160 may be positioned within the bore 64 (see FIGS. 1-3) of the component engaging portion 62 of the first connector 50. At least a portion of the luer fitting 160 comprises an outer diameter that is smaller than an inner diameter of the bore 64, thereby allowing the luer fitting 160 to be at least partially disposed within the bore 64, as shown in FIG. 4. In a next step, the thumb screw 65 may be actuated to cause the threaded portion 66 (see FIG. 2) to be advanced radially inward, thereby engaging an outer surface of the luer fitting 160. This action secures the proximal end 152 of the dilation catheter 150 to the first connector 50.

Similarly, a proximal end 172 of the needle 170 may be coupled to the second connector 70, for example, using a luer fitting 180, which may be positioned within the bore 84 of the component engaging portion 82 of the second connector 70. The thumb screw 85 may be actuated to engage an outer surface of the luer fitting 180, thereby securing the proximal end 172 of the needle 170 to the second connector 70.

In a next step, a portion of the dilation catheter 150 may be inserted into the working lumen 128 of the endoscope 110 and the first connector 50 may then be coupled to the rail member 30. More specifically, the distal end 154 of the catheter 150 (see FIG. 7) may be advanced distally through the adapter 90 and into the working lumen 128 of the endoscope 110, as depicted in FIGS. 4-5. The working lumen 128 of the endoscope 110 may have an inner diameter of about 4.0-5.5 mm, while the overall diameter of the endoscope 110 may be about 10-14 mm. An outer diameter of the catheter 150 may be about 3.0 mm and may comprise a lumen 155 having a diameter of about 1.5 mm. Such dimensions are provided for exemplary reference purposes and are not intended to be limiting.

The distal end 154 of the catheter 150 may be advanced distally within the working lumen 128, for example, until it is disposed just proximal to the distal end 134 of the endoscope 110. During this time, the guide member 58 of the first connector 50 (see FIG. 2) may be aligned and advanced distally within the longitudinally oriented slot 37 of the rail member 30. When positioned at a desired longitudinal location, the thumb screw 55 may be actuated to secure the longitudinal position of the first connector 50. Accordingly, the distal end 154 of the catheter 150 may be securely disposed at a predetermined longitudinal location within the working lumen 128 of the endoscope 110.

Referring still to FIG. 4, the needle 170 then may be disposed through the lumen 155 of the catheter 150 and coupled to the rail member 30. In particular, a distal end 174 of the needle 170 may be loaded in a distal direction through the luer fitting 160 that is coupled to the proximal end 152 of the catheter 150. Then the needle 170 may be advanced distally through the lumen 155 of the catheter 150 until the needle 170 is positioned at a desired location. For example, the distal end 174 of the needle 170 may be advanced distally within the lumen 155 until it is aligned with the distal end of the catheter 155, which may be disposed just proximal to the distal end 134 of the endoscope 110. During this time, the second connector 70 may be aligned with, and advanced distally over, the rail member 30. When positioned at a desired longitudinal location, the thumb screw 75 may be actuated to temporarily secure the positioning of the second connector 70 and the needle 170, as shown in FIG. 4.

The endoscope 110 may be advanced towards a target site within a patient's anatomy using suitable imaging techniques. If an endoscopic ultrasound procedure is performed, the endoscope 110 may be retrofitted with an ultrasound transducer, as noted above. The ultrasound transducer may produce accurate and detailed images, particularly when placed within a certain distance of a desired target site. For example, during a translumenal procedure, the ultrasound transducer may facilitate imaging of a target site in an adjacent vessel or duct when disposed within an original vessel or duct in close proximity to the selected target site. If the distance is too great for use of an ultrasound transducer, then fluoroscopic techniques may be employed, optionally in conjunction with radiopaque bands disposed on the endoscope 110.

During positioning of the endoscope 110, the rail member 30 may be coupled to the auxiliary channel 125 of the endoscope 110, further with the dilation catheter 150 and the needle 170 disposed within the working lumen 128 of the endoscope 110 via the first and second connectors 50 and 70, respectively. In this instance, the dilation catheter 150 and the needle 170 may be pre-positioned within the working lumen 128 of the endoscope 110 during insertion, and therefore, substantially ready for use upon final positioning of the endoscope 110.

Alternatively, the endoscope 110 may be advanced into a patient's body without the dilation catheter 150 and the needle 170 loaded into the working lumen 128 and/or without the rail member 30 coupled to the auxiliary channel 125. For example, the endoscope 110 may be advanced to a desired location within the patient's anatomy. Optionally, a wire guide then may be loaded through the working lumen 128 of the endoscope 110 and advanced towards a target site. The catheter 150 may be advanced distally over the wire guide, through the working lumen 128 of the endoscope 110, and positioned at a desired location. The rail member 30 then may be secured to the endoscope 110 and the longitudinal positioning of the catheter 150 may be secured by coupling the proximal end 152 of the catheter 150 to the rail member 30 using the first connector 50. Subsequently, the wire guide may be proximally retracted and removed from the lumen 155 of the catheter 150. Then, the needle 170 may be distally advanced through the lumen 155 of the catheter 150 and secured in the position shown in FIG. 4 using the second connector 70.

The above-described techniques are exemplary techniques for preparing the dilation catheter 150 and the needle 170 for subsequent use with the endoscope 110 and the rail member 30. Other loading and insertion techniques may be employed to couple the dilation catheter 150 and the needle 170 to the endoscope 110 and the rail member 30.

Figure 6:
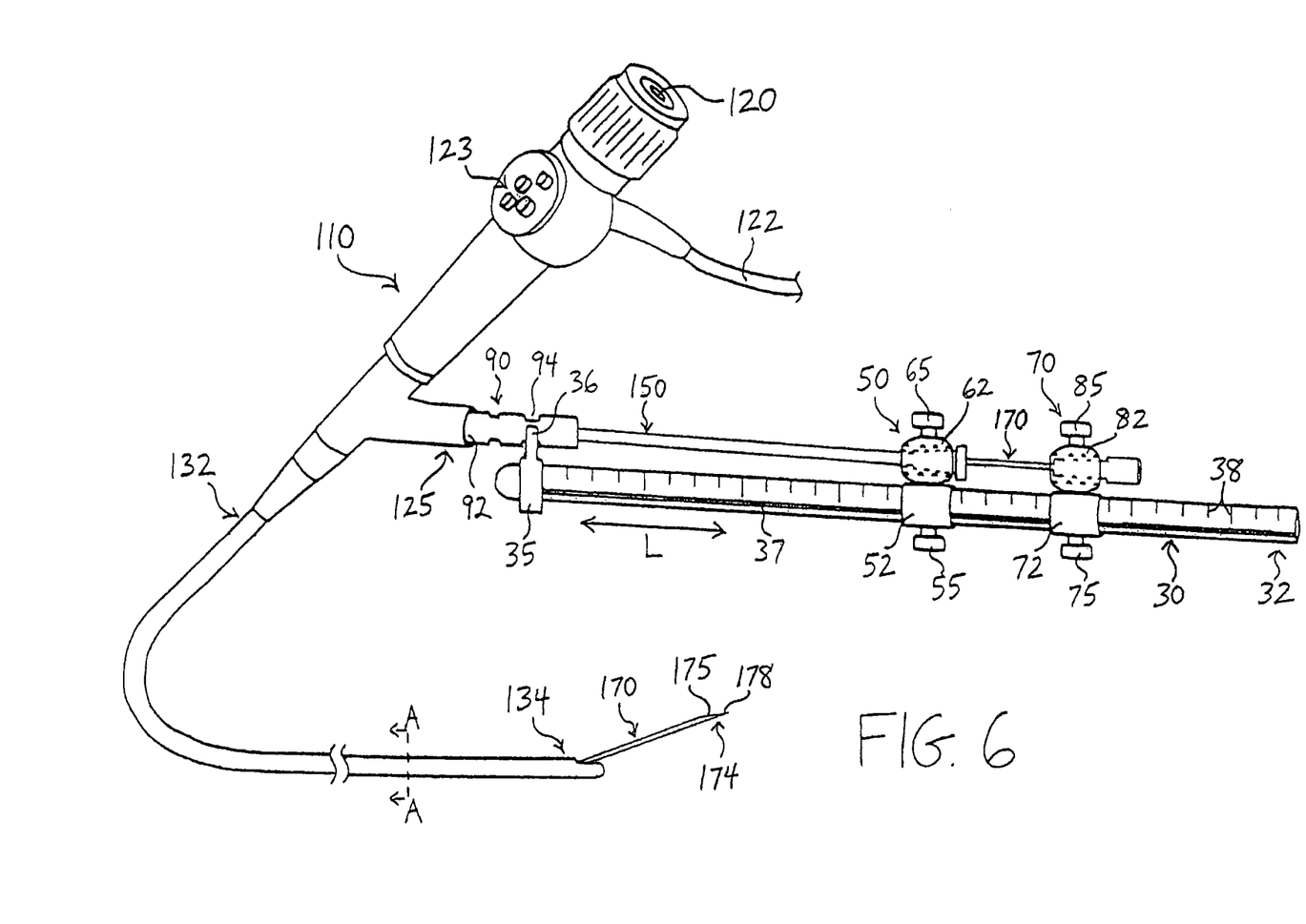
FIG. 6 is a perspective view illustrating the second medical component being advanced with respect to the first medical component.

Referring now to FIG. 6, in a next step, it may become desirable to move the needle 170 a fixed distance with respect to the dilation catheter 150. The thumb screw 75 may be actuated in a direction away from the rail member 30 to permit longitudinal movement of the second connector 70 with respect to the rail member 30. Using the measurement indicia 38, a physician may know exactly how far the second connector 70 is being moved distally with respect to the fixed first connector 50, and therefore, how much the needle 170 is being advanced distally with respect to the dilation catheter 150 and the endoscope 110. As shown in FIG. 6, such distal movement of the second connector 70 may cause the distal end 174 of the needle 170 to extend distally beyond the distal end 134 of the endoscope 110. Using the eyepiece 120, a physician may view the positioning of the distal end 174 of the needle 170.

The distal end 174 of the needle 170 may comprise a sharpened tip 178. Further, the needle 170 may comprise a bore 175 extending between the proximal and distal ends 172 and 174, as depicted in FIGS. 5-6. The needle 170 may comprise an endoscopic ultrasound (EUS) needle, or any other suitable needle. Moreover, the needle 170 may be used for puncturing tissue, obtaining translumenal access, draining cysts or pseudocysts, obtaining tissue samples, providing aspiration, injecting fluids, delivering sclerosing agents or other therapeutic agents, and other purposes.

In one exemplary procedure, the needle 170 may be used for obtaining translumenal access from the gastrointestinal tract to a target site, for example, the celiac plexus. In this case, the distal end of the endoscope 110 may be placed at the appropriate location within the stomach and the needle 170 may be advanced, as shown in FIG. 6, to translumenally pierce through the stomach wall, through the peritoneal cavity, and into the celiac plexus. As will be apparent, many other applications, both translumenal and otherwise, are possible.

Figure 7:
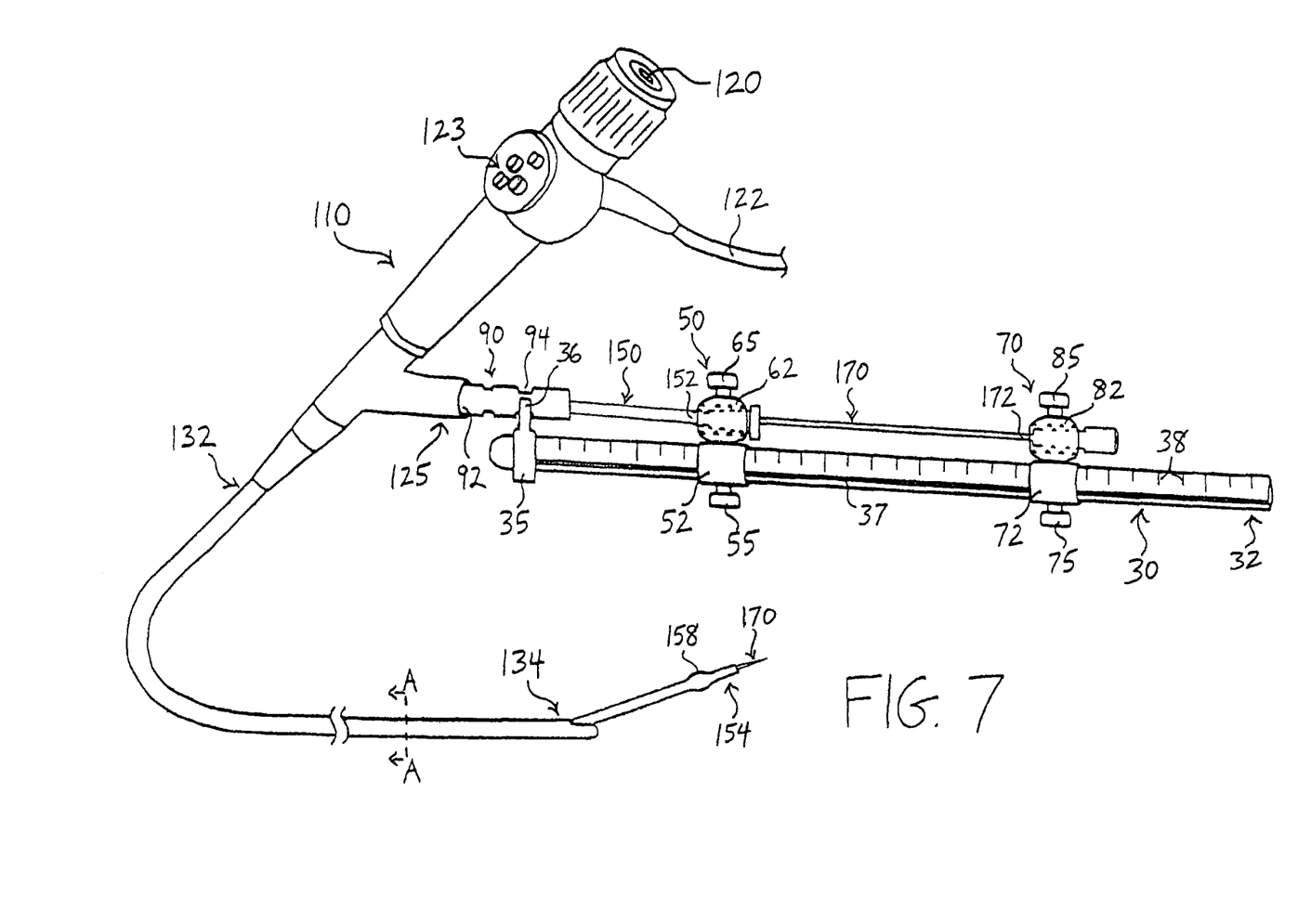
FIG. 7 is a perspective view illustrating the first medical component being advanced with respect to the second medical component.

Referring now to FIG. 7, in a next optional step, it may become desirable to move the dilation catheter 150 a fixed distance with respect to the needle 170 and the endoscope 110. The thumb screw 55 may be actuated in a direction away from the rail member 30 to permit longitudinal movement of the first connector 50 with respect to the rail member 30. Using the measurement indicia 38, a physician may know exactly how far the first connector 50 is being moved distally with respect to the second connector 70 and the endoscope 110. As shown in FIG. 7, such distal movement of the first connector 50 may cause the distal end 154 of the dilation catheter 150 to extend distally beyond the distal end 134 of the endoscope 110. It should be noted that in this configuration, the distal end 154 of the catheter 150 may extend distally beyond the sharpened tip 178 of the needle 170, thereby covering the distal end 174 of the needle 170 and reducing the likelihood of the needle inadvertently cutting tissue.

The distal end 154 of the dilation catheter 150 may comprise a widened section 158, which may be used, for example, to cannulate a body passageway or dilate a stenosis. As will be explained below with respect to FIGS. 9-10, a balloon inflation catheter may be employed in lieu of the dilation catheter 150 shown in the above-described embodiments.

Figure 8:
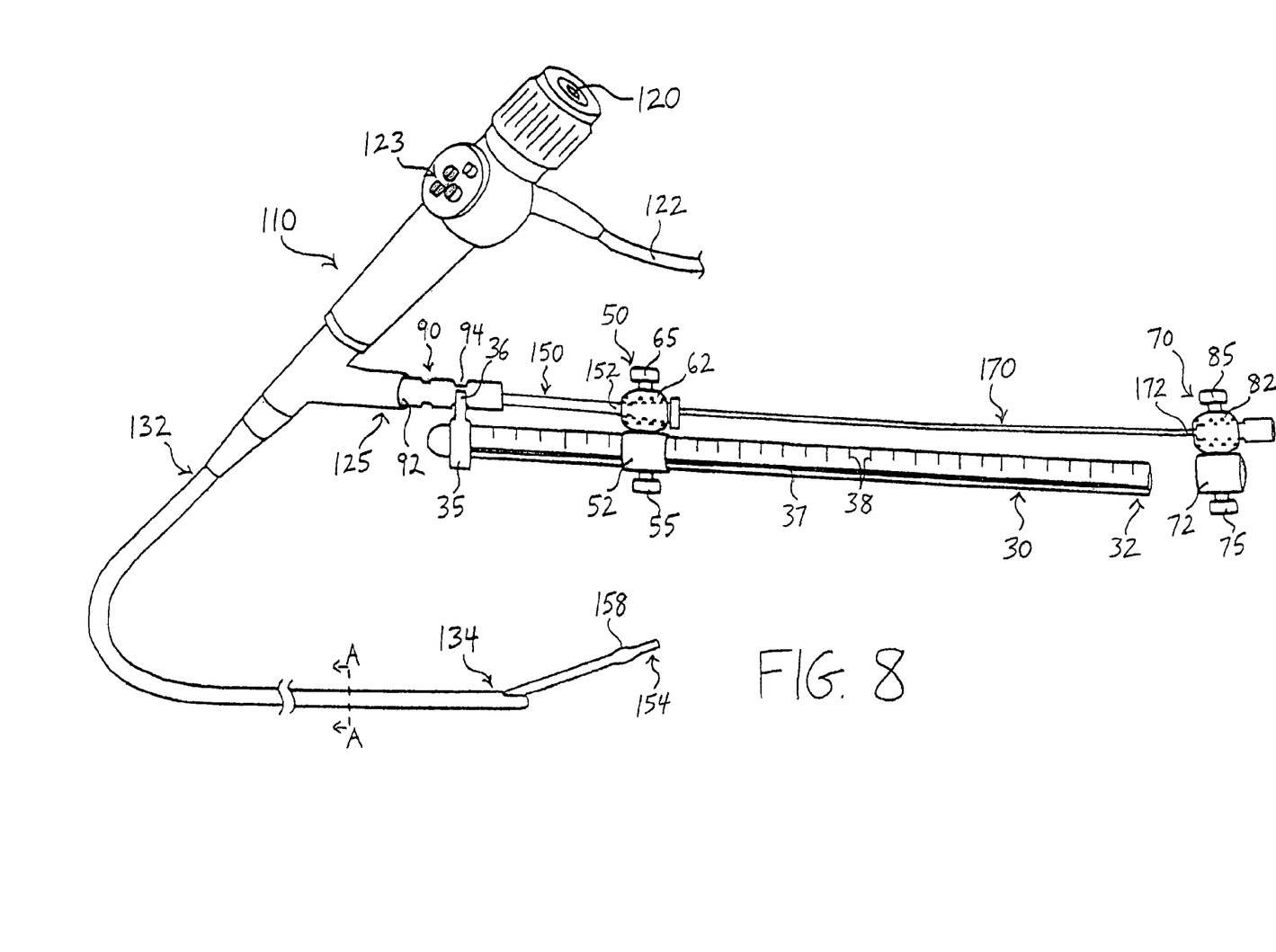
FIG. 8 is a perspective view illustrating the second medical components being removed from the rail member.

Referring now to FIG. 8, once a physician has performed one or more desired procedures using the dilation catheter 150 and/or the needle 170, the needle 170 may be removed from the endoscope 110 and the rail member 30. Specifically, the thumb screw 75 may be actuated to permit longitudinal movement of the second connector 70. The rail engaging portion 72 of the second connector 70 then may be retracted proximally in a linear direction until the second connector 70 is beyond the proximal end 32 of the rail member 30, as shown in FIG. 8. At this time, the second connector 70 further may be retracted proximally to withdraw the needle 170 from the lumen 155 of the dilation catheter 150.

With the needle 170 removed from the lumen 155 of the dilation catheter 150, another component may be introduced through the lumen 155 of the dilation catheter 150. A proximal end of the new component may be coupled to the component engaging portion 82 of the second connector 70, while a distal end of the new component may be inserted through the lumen 155 of the dilation catheter 150.

Further, a suction source may be coupled to the catheter 150 and used to aspirate a cyst or other condition through the lumen 155 of the catheter 150. With the needle 170 having been removed from the lumen 155, a greater diameter of flow is provided to yield enhanced suction capability, which may advantageously drain a cyst in a faster manner.

Alternatively, the dilation catheter 150 also may be removed from the endoscope 110 and the rail member 30. In either case, one or more new medical components may be advanced over the rail member 30 and into the endoscope 110.

In this manner, any number of medical components may be exchanged and used in conjunction with the rail member 30. By coupling proximal ends of the medical components to connectors, such as the first and second connectors 50 and 70, the components may be advanced or retracted a desired distance using the measurement indicia 38. Further, multiple components may be advanced or retracted in a simple linear fashion with respect to one another, and with respect to the endoscope 110.

It should be noted that the second component, which is disposed proximal to the first component on the rail member 30, need not be inserted through a lumen of the first component. For example, in the example of FIGS. 4-8, when the dilation catheter 150 is inserted through the working lumen 128 of the endoscope 110, the needle 170 or other medical device may be advanced adjacent to an outer surface of the dilation catheter 150 within the working lumen 128, as opposed to through the lumen 155 of the dilation catheter 150.

Figures 9, 10:
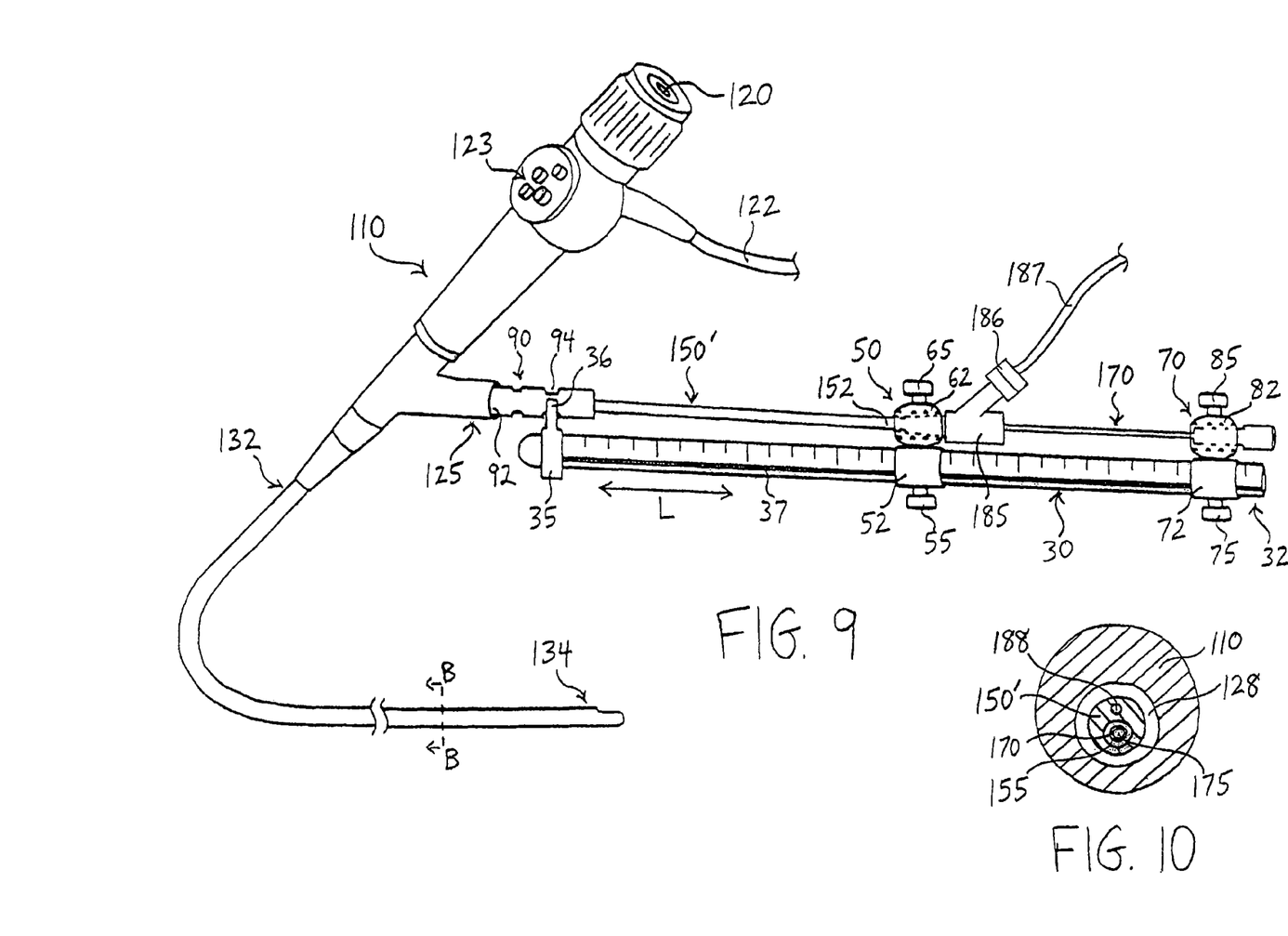
FIG. 9 is a perspective view showing an alternative first medical component, along with a second medical component, being used in conjunction with the apparatus of FIGS. 1-3.
FIG. 10 is a cross-sectional view along line B—B of FIG. 9.

Referring now to FIGS. 9-10, in an alternative embodiment, a balloon inflation catheter 150' may be used in lieu of a non-inflatable dilation catheter 150. The balloon catheter 150' preferably comprises a first lumen 155 for receiving a second component, such as the needle 170, and further comprises a second, inflation lumen 188, as shown in FIG. 10. The inflation lumen 188 is in fluid communication with a balloon coupled to a distal region of the catheter 150'. In use, a Y-shaped connector 185 may be coupled to the proximal end of the balloon catheter 150', as shown in FIG. 9. The second component, such as the needle 170, may be advanced through the Y-shaped connector 185 and into the lumen 155 of the catheter 150'. The other inlet port 186 of the Y-shaped connector 185 may be coupled to an inflation source (not shown) via tubing 187. The inflation source and the tubing 187 are placed in fluid communication with the inflation lumen 188 to permit selective inflation and deflation of the balloon of the catheter 150'. Like the embodiments described above, the first and second connectors 50 and 70 may be advanced or retracted with respect to one another a fixed distance to achieve the objects of a particular medical procedure.

Figure 11:
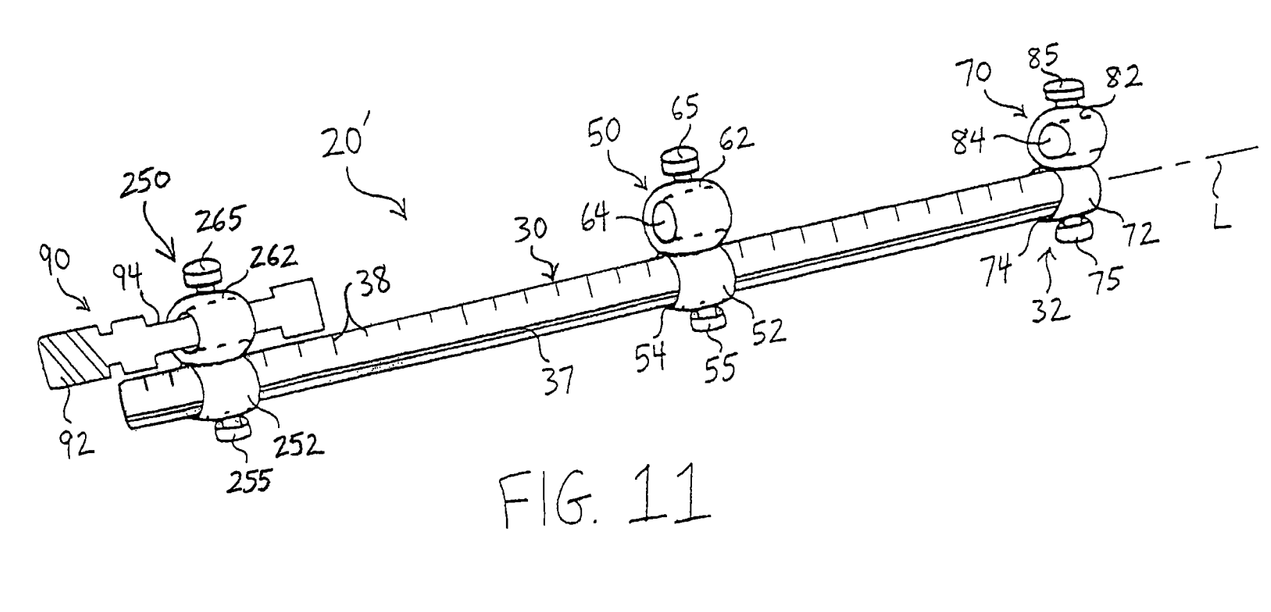
FIG. 11 is a perspective view of an alternative embodiment of apparatus for facilitating positioning of one or more medical components.

Referring now to FIG. 11, an alternative apparatus 20' generally comprises the rail member 30, the first connector 50, and the second connector 70, each of which preferably are provided as described in detail above. The apparatus 20' further comprises an adapter connector 250 in lieu of the fitting 35 above.

The adapter connector 250 preferably is provided in accordance with the first connector 50 and comprises a rail engaging portion 252, an adapter engaging portion 262, and thumb screws 255 and 265. The thumb screw 255, which may be provided in accordance with the thumb screw 55 described above, may be actuated to selectively engage an outer surface of the rail member 30 to selectively permit and inhibit longitudinal movement of the rail member 30 with respect to the adapter 90.

Advantageously, the rail member 30 may be advanced relative to the endoscope 110 when the thumb screw 255 is unscrewed, to thereby simultaneously advance the first and second connectors 50 and 70, along with any associated medical components. By advancing the rail member 30 to simultaneously advance the first and second connectors 50 and 70, the relative positioning of multiple medical components may be maintained. For example, if the dilation catheter 150 and the needle 170 described above are coupled to the first and second connectors 50 and 70, respectively, then advancement or retraction of the rail member 30 via the adapter connector 250 may simultaneously advance or retract the dilation catheter 150 and the needle 170 in tandem. Therefore, in the embodiment of FIG. 11, a physician need not advance two different medical components separately when it is desired to maintain their relative positioning. Notably, the thumb screw 265 may be independently actuated to unlock the adapter connector 250 from the adapter 90.

While two medical components have been shown herein, greater or fewer components and connectors may be employed. For example, only one medical component, and therefore one first connector 50, may be used with the endoscope 110 and the rail member 30. Alternatively, three or more medical components may be used at any given time, in which case three or more associated connectors may be advanced with respect to one another along the rail member 30, or the rail member 30 may be advanced relative to the endoscope 110 in tandem with the three or more associated connectors, as described in FIG. 11.

It will be appreciated that a wide variety of medical components may be used in conjunction with the apparatuses 20 and 20'. For example, catheters, needles, extraction baskets and snares may be delivered using the rail member 30, either alone or in conjunction with one another. Further, self-expanding or balloon-expandable stents may be delivered using the apparatuses 20 and 20'. Still further medical components and applications are intended to be within the scope of the present embodiments. Moreover, while the introducer device has been shown as an exemplary endoscope 110, the apparatuses 20 and 20' may be used in conjunction with various other introducer devices. Still further, it should be noted that Touhy-Borst adapters may be used in conjunction with the apparatuses 20 and 20' to facilitate closure and prevent air from entering into the systems.

While various embodiments of the invention have been described, it will be apparent to those of ordinary skill in the art that many more embodiments and implementations are possible within the scope of the invention. Accordingly, the invention is not to be restricted except in light of the attached claims and their equivalents.

I claim:

1. Apparatus suitable for facilitating positioning one or more medical components, the apparatus comprising:

a rail member having proximal and distal ends and a generally longitudinal axis;

a first connector adapted to be selectively coupled to the rail member and disposed for movement along the generally longitudinal axis of the rail member, wherein the first connector is adapted to be coupled to a first medical component;

a second connector adapted to be selectively coupled to the rail member and disposed for movement along the generally longitudinal axis of the rail member, wherein the second connector is adapted to be coupled to a second medical component; and an adapter coupled to the distal end of the rail member, wherein the adapter is configured to be coupled to a port of an introducer device in order to align the first and second connectors with the port of the introducer device, wherein the rail member is slidably coupled to the adapter such that the rail member, the first connector and the second connector are longitudinally movable, in tandem, relative to the introducer device.

2. The apparatus of claim 1, wherein the introducer device comprises an endoscope and the port enables insertion of the first and second medical components into a working lumen of the endoscope.

3. The apparatus of claim 1, wherein the first medical component comprises a catheter having a lumen.

4. The apparatus of claim 3, wherein the second medical component comprises a needle adapted to be advanced through the lumen of the catheter.

5. The apparatus of claim 4, wherein the needle comprises an endoscopic ultrasound needle.

6. Apparatus suitable for facilitating positioning one or more medical components relative to an introducer device, the apparatus comprising:

a rail member having proximal and distal ends and a generally longitudinal axis, the distal end adapted to be coupled to the introducer device; and a first connector adapted to be selectively coupled to the rail member and disposed for movement along the longitudinal axis of the rail member, wherein the first connector is adapted to be coupled to a first medical component to permit the first medical component to be advanced or retracted relative to the introducer device upon corresponding movement of the first connector along the rail member, wherein the first connector comprises a rail engaging portion and a component engaging portion, wherein the rail member comprises a substantially round cross-sectional profile, wherein the rail engaging portion of the first connector comprises a bore having a greater diameter than an outer diameter of the rail member to permit movement of the first connector over the rail member, and wherein the rail member is slidably coupled to the introducer device such that the rail member and the first connector are longitudinally movable, in tandem, relative to the introducer device.

7. The apparatus of claim 6 further comprising an adapter coupled to the distal end of the rail member, wherein the adapter is configured to be coupled to a port of an introducer device in order to align the first connector with the port of the introducer device.

8. The apparatus of claim 6, wherein the rail engaging portion comprises a guide member adapted for movement within a slot formed in the rail member, thereby substantially inhibiting rotational movement of the first connector with respect to the rail member.

9. The apparatus of claim 6, wherein the component engaging portion comprises a bore adapted to receive a proximal end of the first medical component, and wherein the first medical component is adapted to be securely coupled to the component engaging portion.

10. The apparatus of claim 6 further comprising an actuator for selectively inhibiting longitudinal movement of the first connector with respect to the rail member.

11. The apparatus of claim 10, wherein the actuator comprises a thumb screw.

12. The apparatus of claim 6, wherein the rail member comprises measurement indicia for identifying a distance in which the first connector is advanced or retracted with respect to the rail member.

13. The apparatus of claim 6 further comprising a second connector adapted to be selectively coupled to the rail member and disposed for movement along the generally longitudinal axis of the rail member, wherein the second connector is adapted to be coupled to a second medical component to permit the second medical component to be advanced or retracted upon corresponding movement of the second connector along the rail member, and wherein the second connector is disposed at a location along the rail member proximal to the first connector.

14. The apparatus of claim 6 wherein the component engaging portion comprises a bore adapted to receive a proximal end of the first medical component, and wherein the first medical component is slidably movable within the bore of component engaging portion.

15. The apparatus of claim 6 further comprising an adapter coupled to the distal end of the rail member, wherein the adapter comprises a male luer lock adapter, and wherein the adapter is secured at least partially within a port of the introducer device in order to align the first connector with the port of the introducer device.

16. A method suitable for facilitating positioning one or more medical components, the method comprising:

providing a rail member having proximal and distal ends and a generally longitudinal axis;

coupling a first connector to the rail member;

coupling a first medical component to the first connector;

coupling a second connector to the rail member;

coupling a second medical component to the second connector; and coupling an adapter to the distal end of the rail member and to a port of an introducer device to align the first and second connectors with the port of the introducer device, wherein the rail member is slidably coupled to the adapter such that the rail member, the first connector and the second connector are longitudinally movable, in tandem, relative to the introducer device.

17. The method of claim 16, wherein the first connector comprises a rail engaging portion and a component engaging portion, the method further comprising coupling the first medical component within a bore of the component engaging portion.

* * * * *